United States Patent [19]
Accorsi et al.

[11] Patent Number: 5,234,837
[45] Date of Patent: Aug. 10, 1993

[54] PSEUDO-CONTINUOUS PROCESS FOR INTERROGATING A COMBUSTIBLE GAS DETECTOR

[75] Inventors: Antoinette Accorsi, Pont-Sainte-Maxence; Andrée Wattier, Verberie; Marc Kazmierczak, Maysel, all of France

[73] Assignee: Charbonnages de France, Malmaison, France

[21] Appl. No.: 768,301

[22] PCT Filed: Apr. 5, 1990

[86] PCT No.: PCT/FR90/00242
§ 371 Date: Oct. 7, 1991
§ 102(e) Date: Oct. 7, 1991

[87] PCT Pub. No.: WO90/12313
PCT Pub. Date: Oct. 18, 1990

[30] Foreign Application Priority Data
Apr. 6, 1989 [FR] France .................... 89 04547

[51] Int. Cl.⁵ ............................................. G01N 25/22
[52] U.S. Cl. .................... 436/159; 73/23.31; 422/94; 422/98
[58] Field of Search ............... 422/94, 98, 97; 436/159; 73/23.31; 324/204

[56] References Cited
U.S. PATENT DOCUMENTS

| | | | |
|---|---|---|---|
| 1,231,045 | 6/1917 | Means | 422/94 |
| 3,200,011 | 8/1965 | Baker | 422/94 |
| 3,911,386 | 10/1975 | Beaudoin et al. | 422/94 |
| 4,538,448 | 9/1985 | Boutonnat et al. | 422/94 |
| 4,870,025 | 9/1989 | Hurley et al. | 422/97 |
| 4,992,384 | 2/1991 | Laurs et al. | 436/159 |

Primary Examiner—Robert J. Warden
Assistant Examiner—Hien Tran
Attorney, Agent, or Firm—Browdy and Neimark

[57] ABSTRACT

To measure the concentration in a gaseous medium of a known combustible gas a resistive element in the gaseous medium having a catalytic surface or being sensitive to variations in the concentration of the combustible gas in the gaseous medium is electrically heated, the value of a parameter representative of the gas concentration is detected and there is deduced therefrom, using a conversion law obtained previously by calibration, a measurement of said concentration. The element is heated periodically in cycles comprising a heating phase, a second phase in which the intensity I is controlled in such a way as to maintain the resistive element at a set point temperature and the stabilized value of the voltage U at the terminals of the detector is measured, and a third phase in which the heating power is reduced. On average the power of the electric current flowing during the second phase is substantially less than the heating current power.

12 Claims, 13 Drawing Sheets

PSEUDO-CONTINUOUS PROCESS FOR INTERROGATING A COMBUSTIBLE GAS DETECTOR

The present invention concerns detecting combustible gas in a gaseous medium such as air.

A known method of detecting combustible gas in air uses a sensor device, generally called a catalytic filament explosimeter, in which a filament, usually of platinum, is heated by the Joule effect, in other words by passing an electric current through it. The combustible gas contained in the surrounding air oxidizes by catalysis in contact with the filament, so that the filament temperature increases. This increases the resistance of the filament, which is measured directly or indirectly to determine the concentration of said combustible gas in the air.

To give one example, the applicant has proposed in French patent FR-1.444.771 filed 4 May 1965 apparatus for sampling and measuring gas in the air in which the gas is metered by measuring the voltage across one diagonal of a resistive bridge comprising a detector filament and a compensator filament connected in parallel with two resistors, one of which is advantageously a variable resistor.

The applicant has also proposed in French patent FR-1.577.448 filed 22 May 1968 a method and apparatus for measuring a parameter characteristic of a gaseous medium in which the value of the parameter in question is estimated by measuring power supply data for a detector filament when the resistance of the filament is held equal to that of a compensator filament.

The applicant has also proposed in French patent FR-1.576.576 filed 6 Jun. 1968 a method and apparatus for metering combustible gas in which a substantially constant voltage is maintained across the filament despite variations in its resistance due to wear or the presence of combustible gas.

Similarly, the applicant has disclosed in French patent FR-1.579.535 filed 21 Mar. 1968 a voltage stabilizer circuit for supplying metering filaments at a substantially constant voltage.

More recently the applicant has proposed in French patent FR-2.537.722 filed 14 Dec. 1982 a measuring method and apparatus designed to eliminate the effects of diffusion of combustible gases in the air and making it possible to eliminate the effects of differences in oxidization heat between gases. To this end the changing value of a parameter representative of the supply of power to the filament is measured, the supply of power being controlled in such a way as to hold the filament resistance constant.

Although the use of a filament to catalyze combustion of methane now makes it possible to monitor very accurately the presence of methane in a mine, the power supply and measuring arrangements used until now have the disadvantage of relatively rapid ageing and relatively high electrical power consumption, making intermittent use necessary and so increasing the real response time.

In an attempt to alleviate these disadvantages other equipment has been based on catalytic beads comprising a metal detector (made of platinum, for example) coated with doped alumina and resembling a small pearl.

Use of these catalytic beads has made possible continuous monitoring of combustible gas levels through slower ageing linked to a lower combustion temperature. However, these beads suffer from significant drift in sensitivity, decreased stability and a longer response time than filaments.

An object of the invention is to alleviate the aforementioned disadvantages and to provide a new filament interrogation method with reduced electrical power consumption, slower ageing and pseudo-continuous use, that is to say use which is continuous as far as can be perceived by the user, the interrogation cycle time being much shorter than the sensor response time.

To this end the invention proposes a method for measuring the concentration in a gaseous medium of a known combustible gas in which method a resistive element in the gaseous medium having a catalytic surface or being sensitive to variations in the concentration of the combustible gas in the gaseous medium is electrically heated, the value of a parameter representative of the gas concentration is detected and there is deduced therefrom, using a conversion law obtained previously by calibration, a measurement of said concentration of the combustible gas in the gaseous medium, characterized in that, with a predetermined interrogation period, the resistive element is supplied with power in cycles comprising three phases:

in a first phase there flows in the resistive element a heating current adapted to raise its temperature within a predetermined heating time to a predetermined set point temperature such that the catalytic surface of the resistive element catalyzes combustion of said combustible gas, in a second phase the resistive element is further supplied with electric current for a predetermined regulation time during which the intensity is controlled so as to maintain the temperature of the resistive element at the set point temperature and, when the voltage $U_D$ across the resistive element has stabilized, the value of the parameter representative of the gas concentration is measured and said measured combustible gas concentration is deduced therefrom, the power of the electric current flowing during this second phase being on average substantially less than the power of the heating current, and in a third phase the resistive element heating power is reduced to allow it to cool to a quiescent temperature.

The supply of electrical power may advantageously be cut off during the third phase.

The parameter representative of the gas concentration is preferably the resistance of the detector.

By starting in this way with a high electrical power heat losses are reduced, in particular losses by conduction along supports of the resistive element or along the element itself.

The method of the invention is based on the applicant's discovery that the resistive filament withstands the high current without damage and that the catalytic reaction with the gas occurs in a very short time (around 0.15 s).

By this method the temperature needed to oxidize the gas is reached very quickly, limiting heat loss into the environment, which significantly reduces the electrical power consumption.

What is more, in this method the oxidization of the gas does not alter in any way the thermal equilibrium of the sensor with its environment, so shortening the response time. Thus the sensor functions for each interrogation for a shorter time at a high temperature and its service life is increased; it is therefore possible to increase the interrogation frequency and to take the measurements at shorter intervals, for example every three seconds or even less.

According to preferred features of the invention:
the maximum interrogation period is four seconds;
the total duration of the first and second phases is less than 300 ms;
the duration of the first phase is less than 200 ms;
the set point temperature is at least equal to the temperature at which the gas begins to react with the resistive element or with the element carried by the resistive element;
for a platinum-based catalytic resistive element the set point temperature for methane is between 570° C. and 1,100° C., preferably between 900° C. and 1,100° C.;
the set point temperature is substantially equal to 1,000° C.;
the average heating power is between a value equal to and an integer multiple value of the electrical power of the second phase, said integer multiple being compatible with the durability of the resistive element (in practice less than 10); this ratio is preferably between 1 and 3;
the power supply intensity is advantageously constant during the heating phase.

The second phase in which the temperature of the resistive element is maintained constant may be implemented in various ways:
by maintaining the resistance constant, to be explained later,
by maintaining constant at a given value the ratio of the resistance associated with the temperature during the second phase to the resistance associated with the quiescent temperature (third phase); this value is between 1.1 and 4, for example,
or by any means of controlling this temperature enabling the heating current to be controlled.

In one preferred embodiment of the invention the nature of the gas is determined by measuring the time for the resistive element to reach thermal equilibrium and with reference to predetermined correlations, for various possible values of relative humidity of air and various possible gases, between the time for the resistive element to reach thermal equilibrium and the concentration of the gas concerned.

Objects, characteristics and advantages of the invention will emerge from the following description given by way of example with reference to the appended drawings in which.

Figure 1:
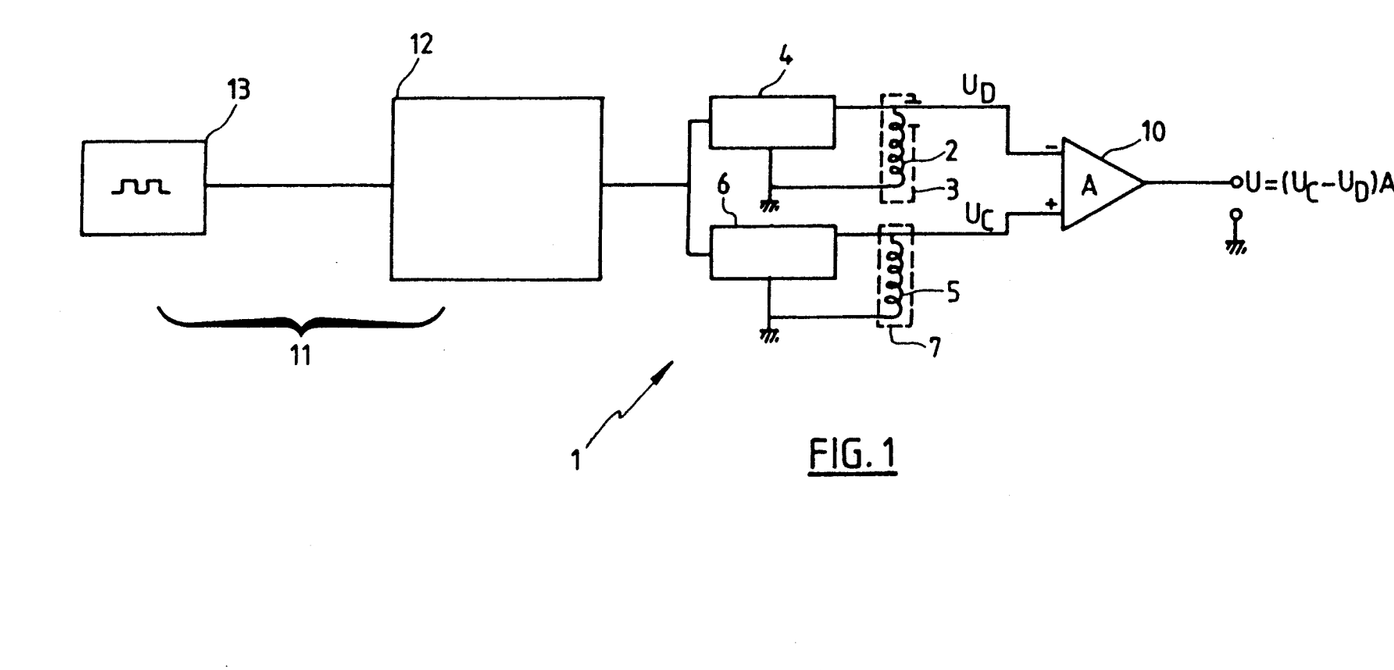
FIG. 1 shows the general schematic of a device for implementing the measuring method of the invention.

FIG. 1 shows a combustible gas detection device 1 including a platinum-based (for example) catalytic surface resistive element 2 forming a detector designed to be placed in a gaseous medium to be tested, being contained in a measuring cell 3 open to the exterior, for example.

The resistive element is a platinum filament, for example, in practice a spirally wound filament 80 μm in diameter in cross-section and 1 cm long. In an alternative implementation (not shown) the resistive element is incorporated in a catalytic bead. It is even feasible for the catalytic surface of the resistive element to be in a material different from that of the remainder of the resistive element.

Between the terminals of the resistive element 2 is a control device 4 of any known kind able to control the supply of power to the element 2 in such a way as to maintain the resistance constant.

The resistive element 2 forming the detector is preferably associated with a second resistive element 5, for example (as here) also platinum-based and identical to the element 2, between the terminals of which there is also connected a control device 6 of the same kind as and having the same function as the control device 4. The second resistive element 5 is disposed in a gaseous medium similar to the gaseous medium to be tested except that there is no combustible gas, this medium being enclosed in a second measuring cell 7 near the cell 3. The second resistive element constitutes a compensator for eliminating the effects of external temperature and wear of the filaments (which are changed at the same time).

An appropriate known type operational amplifier 10 is provided to compute the different U (subject to a multiplication coefficient A) between the respective voltages $U_D$ and $U_C$ between the terminals of the detector resistive element 2 and the compensator resistive element 5. This difference U can be sent to a display device such as an oscilloscope, a transmitter, a temporary store or even a comparator device adapted to trigger an alarm if the difference U exceeds a predetermined threshold (not shown here).

The control devices 4 and 6 are supplied with power by a power supply unit 11 comprising a conventional voltage generator 12 (5 V supply to the resistive element and the compensator element and ±15 V supply to the amplifier) preceded by a "Wavetek model 801 Pulse Generator" type sequencer 13 for programming the time of each interrogation and the quiescent time between two interrogations at the required frequency.

Figure 2:
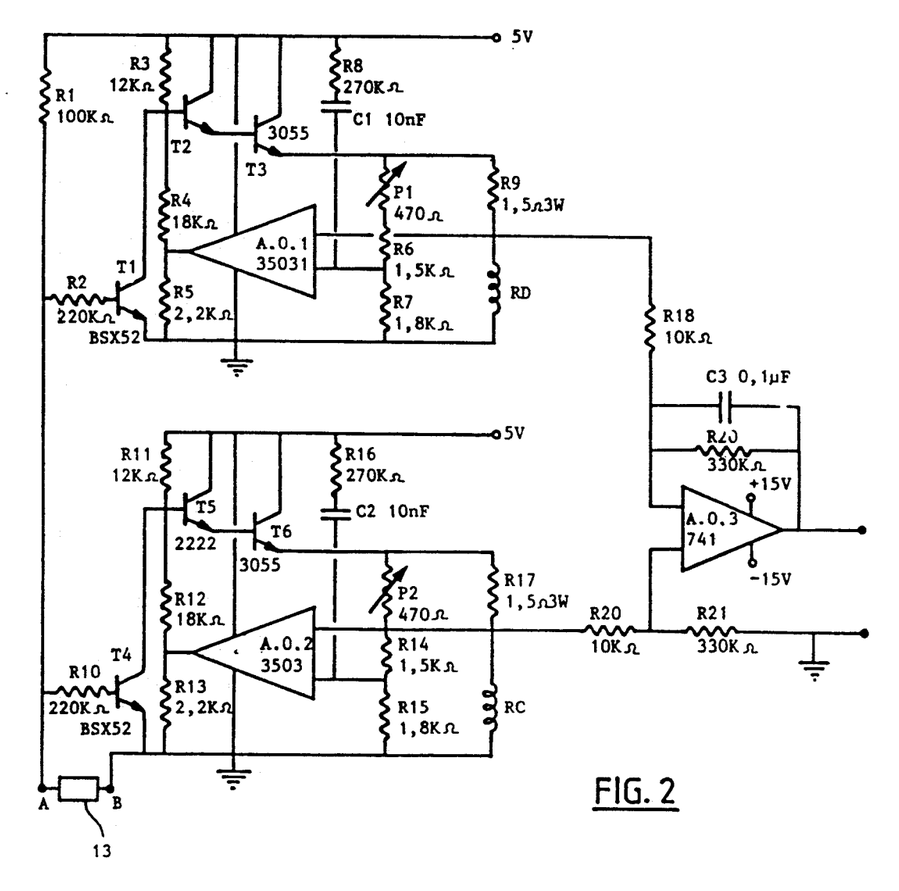
FIG. 2 shows the schematic of the control device of the detector that this device incorporates.

FIG. 2 shows by way of non-limiting example the schematic of the control devices 4 and 6. Each control device includes a resistance bridge supplied through transistors by the sequencer 13 connected between the points A and B and supplying at A a voltage of at least 1 V.

In FIG. 2 the values alongside each component are those for a conventional platinum filament 1 cm long and 80 μm in diameter.

It will be noted that this system speeds up the heating of the filaments as it holds them at an increased voltage until the required temperature is reached.

The operational amplifier A.0.3 is used in a conventional differential circuit in which the capacitor C3 eliminates spurious signals at frequencies above 5 Hz.

The two control devices are identical. Consider how the first operates:

A high level (absence of signal at "A") turns on the transistor T1. The transistors T2 and T3 are therefore turned off and no current flows through the filaments.

A low level at "A" turns off T1. T2 and T3 controlled by A.0.1 control the current in the resistive bridge (P1, R6, R7, R9, RD) in such a way that RD assumes the value (R9×R7)/(P1+R6). The potentiometer P1 varies this value. R8 and C1 eliminate oscillation due to the thermal inertia of the filament.

An oscilloscope is used to measure the voltage between the terminals of the detector and compensator filaments and across the resistors R9 and R17. The measured values are then transferred to a recording device.

The voltage across the resistors is used to determine the current in the detector and the compensator; knowing the voltage across the latter, it is possible to deduce the resistance of the filaments and therefore their temperature.

The output of the operational amplifier A.0.3 is set to zero in air and serves to measure the difference between the two control devices in the presence of methane. Those skilled in the art will know how to use a device to interrogate the filament to program the interrogation time and the quiescent time between two interrogations at the required frequency.

Figure 3:
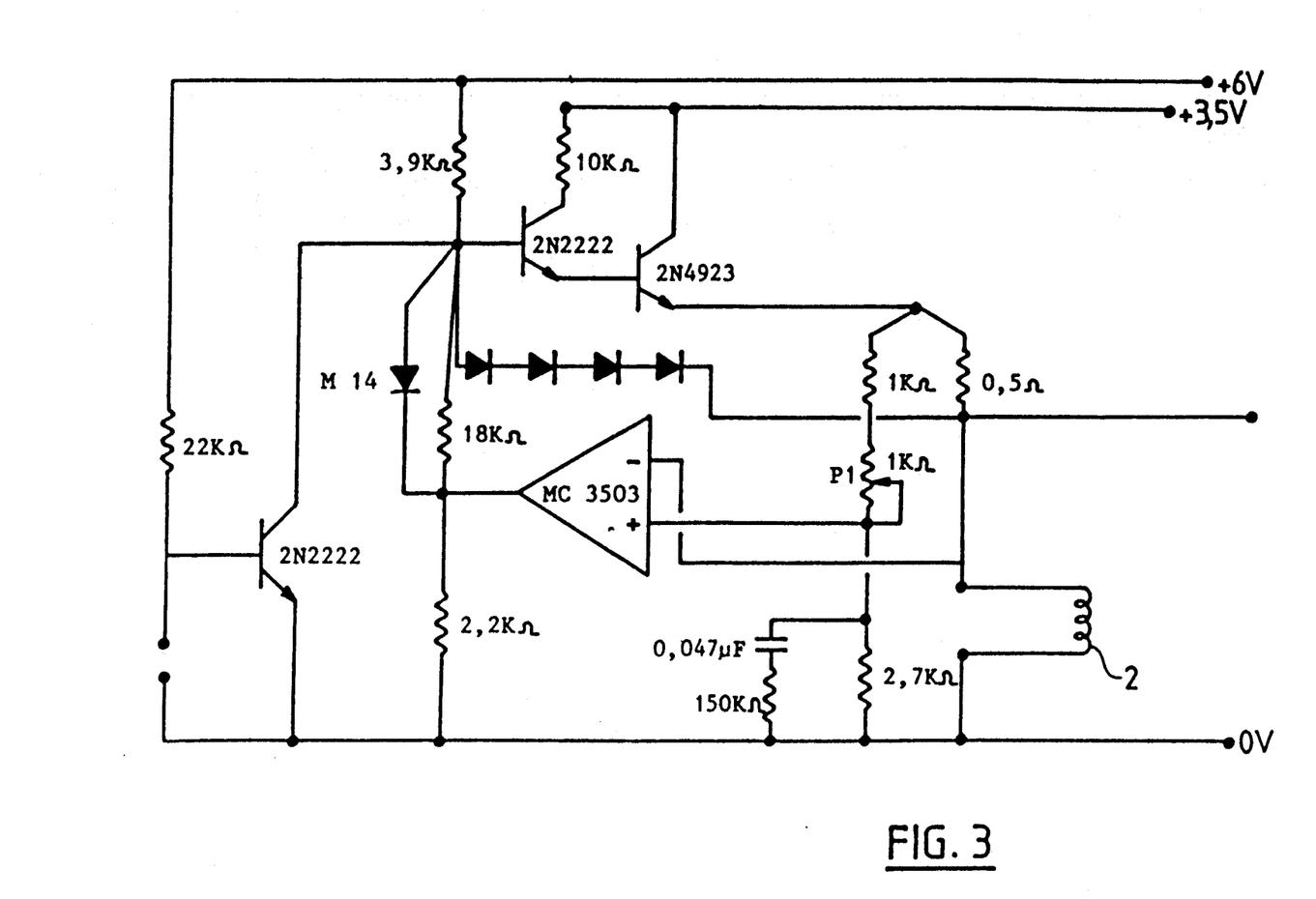
FIG. 3 is a variant of FIG. 2.

FIG. 3 is a variant implementation of the control device 4 or 6. It differs from that of FIG. 2 in that the current remains constant throughout the temperature increase phase and at a value higher than that resulting from the electrical schematic shown in FIG. 2. To this end the power supplies are split, one supplying the resistive element (at 3.5 V) and the other the circuit as a whole (at 6 V).

Also, the compensator 5 and its control device are eliminated and the voltage across the resistive element 2 is monitored.

In accordance with the invention, the device from FIG. 1 is used to heat the detector 2 (and the compensator 5, when included) in two phases:

in a first phase a high heating current is caused to flow until the resistive element 2 (and the element 5 when present) reaches a predetermined set point temperature;

in a second phase the current is controlled to maintain the resistive element at the set point temperature (for example, to maintain the resistance of the resistive element at the value associated with the set point temperature, for example 1.2 ohms at 1,000° C. in the case of a filament 1 cm long and 80 μm in diameter).

The intensity of the heating current is chosen to be significantly higher than the average intensity for the second phase (preferably between two and three times this average intensity in practice). This saves time and reduces the electrical power requirement by reducing the associated heat losses by conduction. It shortens the subsequent cooling time before the next interrogation. The heating is advantageously approximately constant, but a higher energy pulse of more or less controlled form may equally well be used.

If a combustible gas oxidizes in contact with the detector resistive element 2, it transfers heat energy to the element, whose temperature will tend to rise; to compensate for this, the control device 4 will supply less electrical energy by reducing the current through it: this results in a drop in the voltage across it which, after stabilization during the second phase, is representative of the gas concentration.

In the case of a platinum filament 1 cm long with an 80 μm diameter cross-section the set point temperature is advantageously around 1,000° C. In theory a temperature of 570° C. would be sufficient to catalyze the reaction with methane (to take the classical case of gases to be monitored in coal mines), but the electronic circuits for amplifying the signal are then very costly. An only slightly higher temperature (600° to 800° C.) would alleviate this disadvantage in part, but the cost of the associated electronics would remain very high. A much higher temperature (more than 1,200° C.) would cause excessively fast wear of the filament. A temperature between 800° and 1,200° C., or, even better, between 900° and 1,100° C., is found to represent an optimum compromise from the points of view of overall size, cost and durability. For example, 1,000° C. and 1,200° C. respectively correspond to voltages across the resistive element of around 0.76 V and 0.9 V.

To reduce the total time for which the power is supplied (the combination of the two phases as previously described) and therefore the duration of the subsequent cooling period and so increase the interrogation frequency to the point at which the measurement process appears continuous it is necessary to damp the supply voltage in the second phase as quickly as possible after the end of the heating phase; to this end the value of the components C1 and R8 in FIG. 2 may be adjusted, if necessary, to suit the specific characteristics of the filament concerned, the nature of the gas to be monitored and the ranges of concentration in which it is to be monitored. The values shown in FIGS. 2 and 3 correspond to a methane concentration of 0 to 3% for a platinum filament 1 cm long with a cross-section 80 μm in diameter manufactured by Oldham under a Cherchar licence.

To meet the objective of an apparently continuous measuring process, the repetition period of the interrogation cycles is advantageously not more than about four seconds, preferably less than or equal to three seconds.

For set point temperatures of 900° C. to 1,200° C. the total duration of each interrogation cycle is advantageously less than 400 ms, and preferably equal to (or less than) 300 ms, broken down into 200 ms heating and 100 ms stabilization before measuring. The heating intensity is advantageously between 1 A and 2 A (around 1.3 A, for example) while the average intensity in the control-stabilization phase is between 0.65 A and 0.75 A (around 0.7 A, for example).

Figure 4:
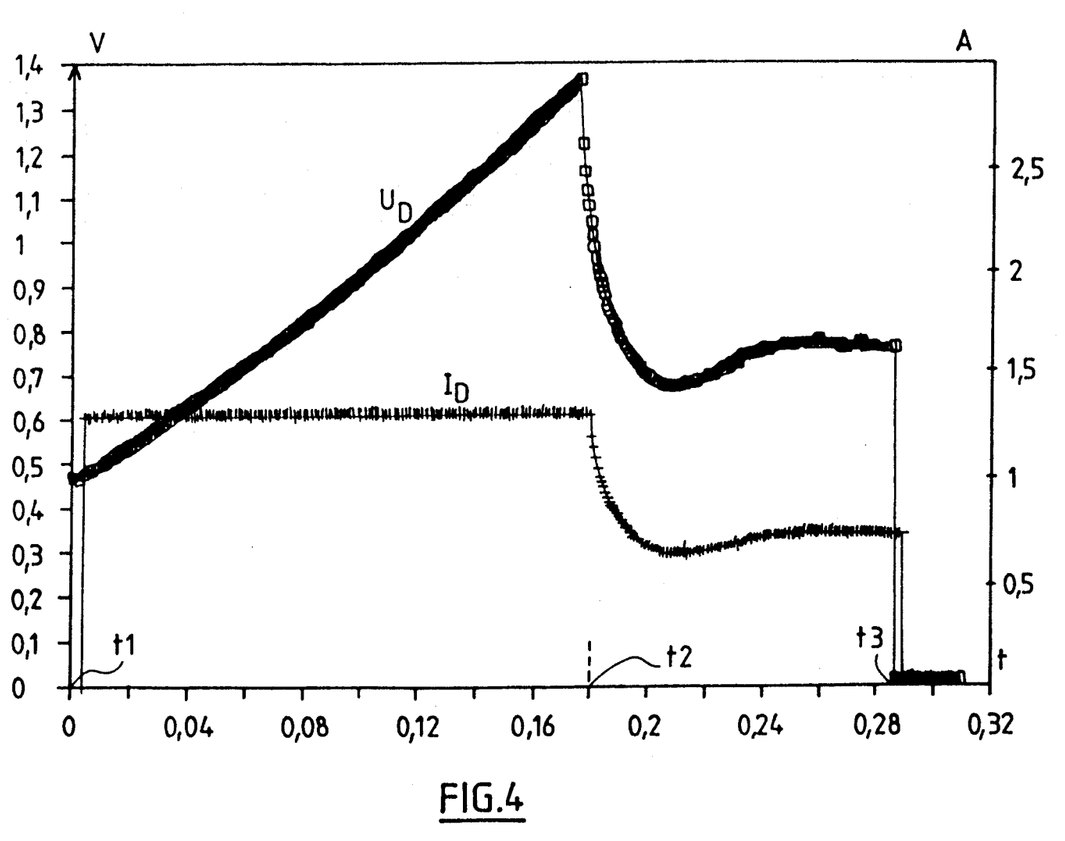
FIG. 4 is a graphical representation of the detector supply current $I_D$ and the voltage $U_D$ across the detector plotted as a function of time during one interrogation cycle.
Figure 5:
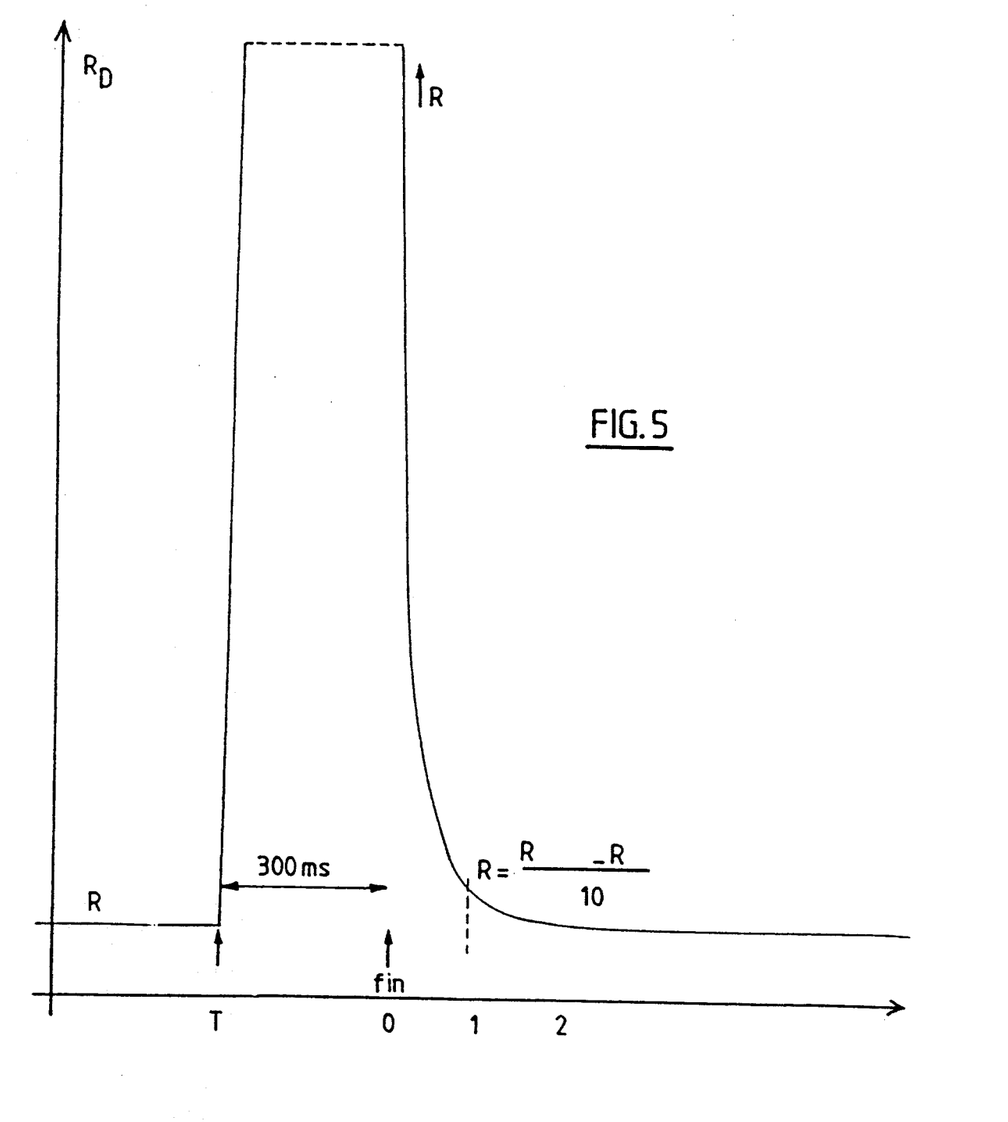
FIG. 5 is a graphical representation showing the filament resistance as a function of time during the filament interrogation and cooling phases.

FIGS. 4 and 5 respectively show the intensity $I_D$ and the voltage $U_D$ (FIG. 4) and the resistance $R_D$ (FIG. 5) plotted as a function of time for the detector. With an interrogation period of four seconds there is a heating phase of approximately 200 ms and a control phase of approximately 100 ms in the case of platinum filament (1 cm long, 80 μm in diameter) at a set point temperature of 1,000° C. (corresponding to a resistance of 1.3 ohms).

During the first phase the intensity $I_D$ is approximately 1.3 A and the voltage $U_D$ varies in a quasilinear manner between 0.47 V and 1.37 V. During the control phase the intensity fluctuates around 0.6 A while $U_D$ stabilizes at a value (less than 0.76 V) characteristic of the methane concentration.

After the supply of power is interrupted, the resistance returns to a value R very close to its initial value $R_{initial}$ after two seconds.

The various advantages of this method result from the reduced operating stresses on the filament:
electrical power consumption reduced by a factor of 2 or 3,
decreased response time,
increased interrogation frequency,
increased filament life.

In this way:
for platinum filament sensors interrogated intermittently in the conventional way the filament is supplied at 0.76 V with a current of 0.8 A for 4 s so that the energy consumed is $E = V.i.t = 2.4$ Joules and the power consumption is $P = E/t = 600$ milliwatts;

for filament sensors supplied with power by the new method in accordance with the present invention the filament carries a constant current of 1.3 A for 200 ms to heat it to its operating temperature and then operates at constant temperature (and resistance) with a voltage across it of around 0.76 V for 100 ms.

While the temperature is increasing, the average resistance is 0.8 ohm (linear increase in temperature, therefore in resistance). During the constant temperature phase the resistance is 1.3 ohms.

The energy consumed is therefore:

$E = R1.I^2.t1 + (V2/R2)t2$ $E = 0.8 \times 1.69 \times 0.19 + (0.5776/1.3) \times 0.1$ $E = 300$ mJ $P = 75$ mW (as the measuring frequency is one measurement every four seconds).

If the current in the temperature increase phase is 2 A the duration is only 60 ms. In this case the energy consumed is reduced to:

$E = 200$ mJ and $P = 50$ mW.

Figure 6:
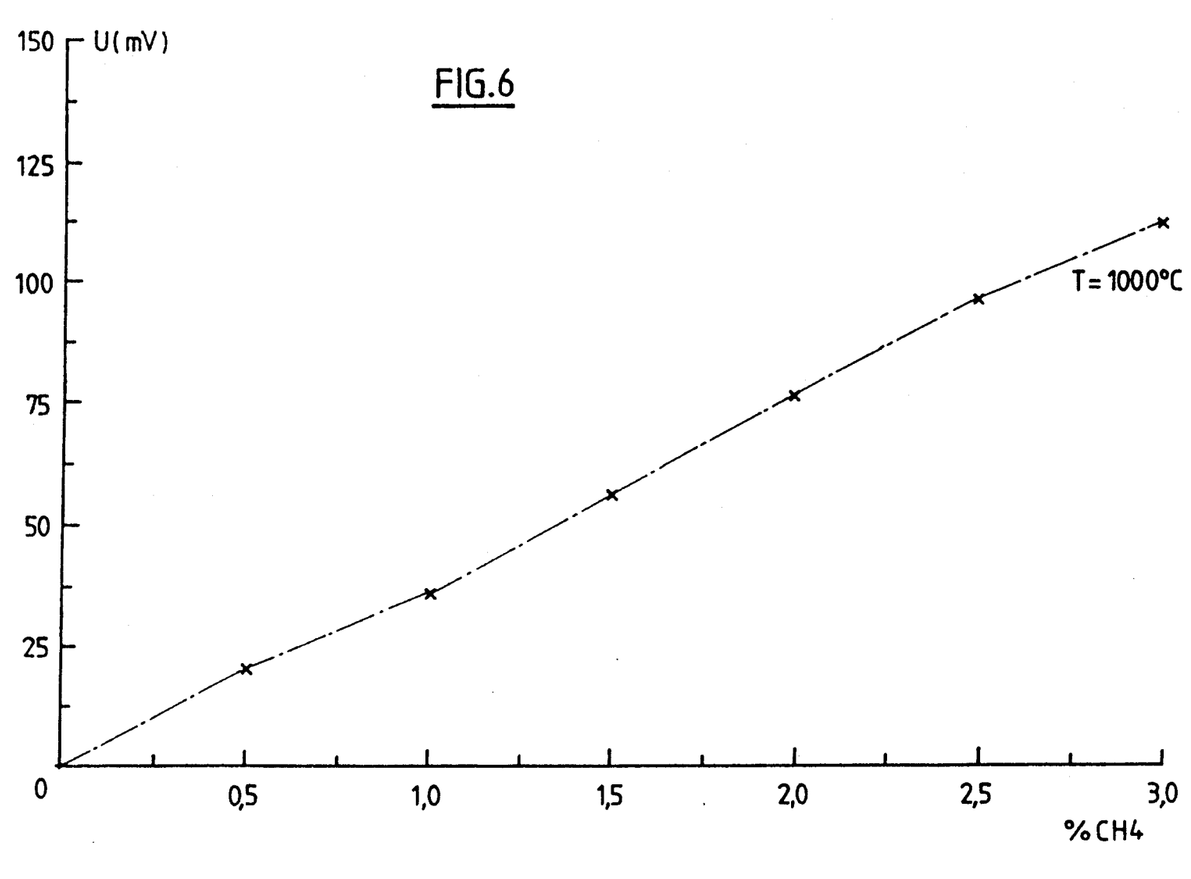
FIGS. 6 and 7 are graphical representations of the signal voltage (voltage in air-voltage in the presence of gas) plotted as a function of the combustible gas concentration (for two separate filaments)
Figure 7:
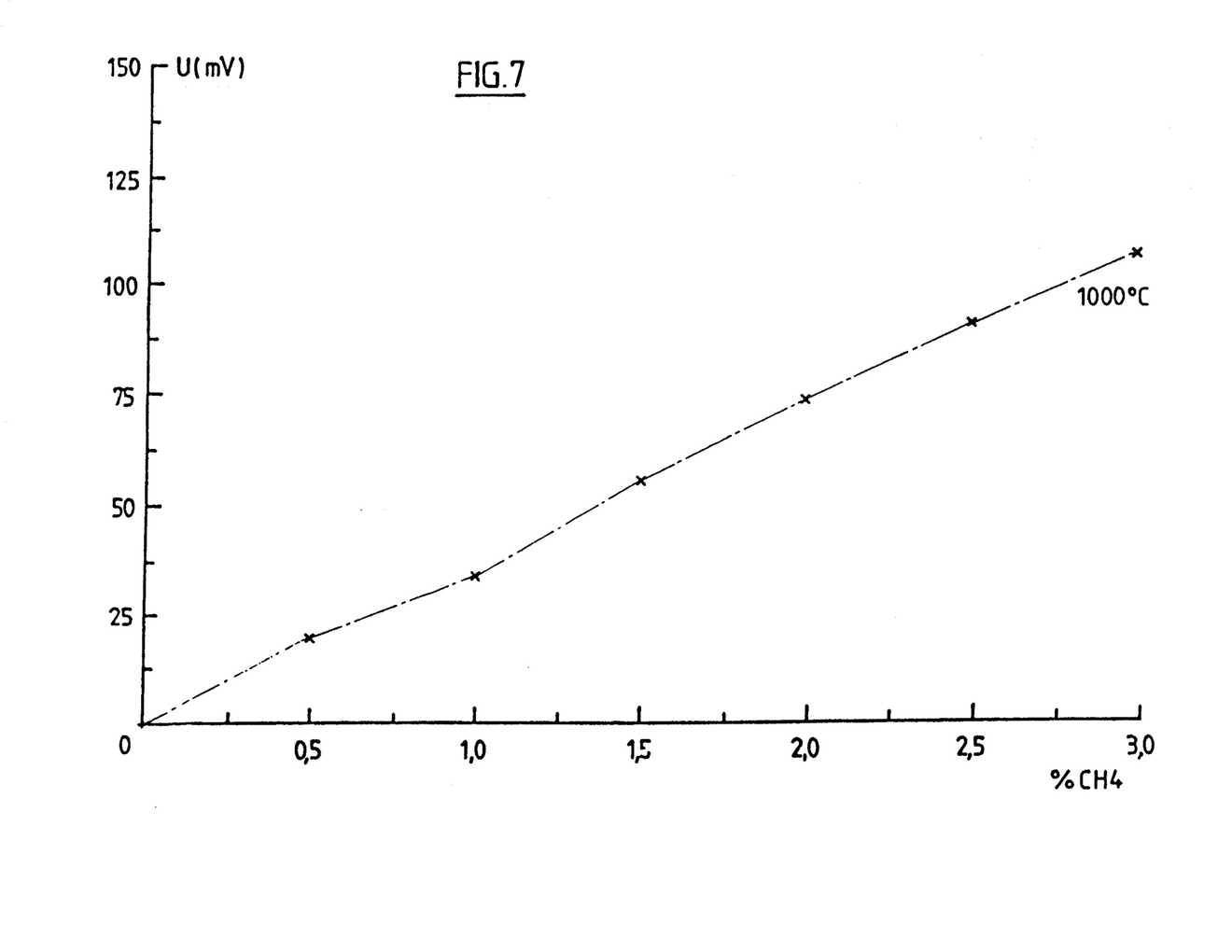

FIGS. 6 and 7 show that the signal is linear for low concentrations (0 to 3%) of an explosible gas, so that for use as an explosimeter the signal processing can be simplified.

The measurements are taken using a high-speed recording device connected to the terminals of the filament (detector or compensator); the output of the operational amplifier A, which is set to zero in air, is indicative of the difference between the voltages at the output of the two control devices in the presence of the combustible gas. The calibration curves are established in any appropriate manner.

FIGS. 8 through 12 show an application of the invention firstly to recognition and then to quantitative detection of combustible gases.

Referring again to FIG. 4, note that between the times $t_1$ and $t_2$ the filament reaches thermal equilibrium which is maintained between times $t_2$ and $t_3$.

The time $t_2 - t_1$ to reach thermal equilibrium depends on parameters relating to the filament (its nature and geometry) and to the nature of the gas contributing to the thermal exchanges.

Figure 8:
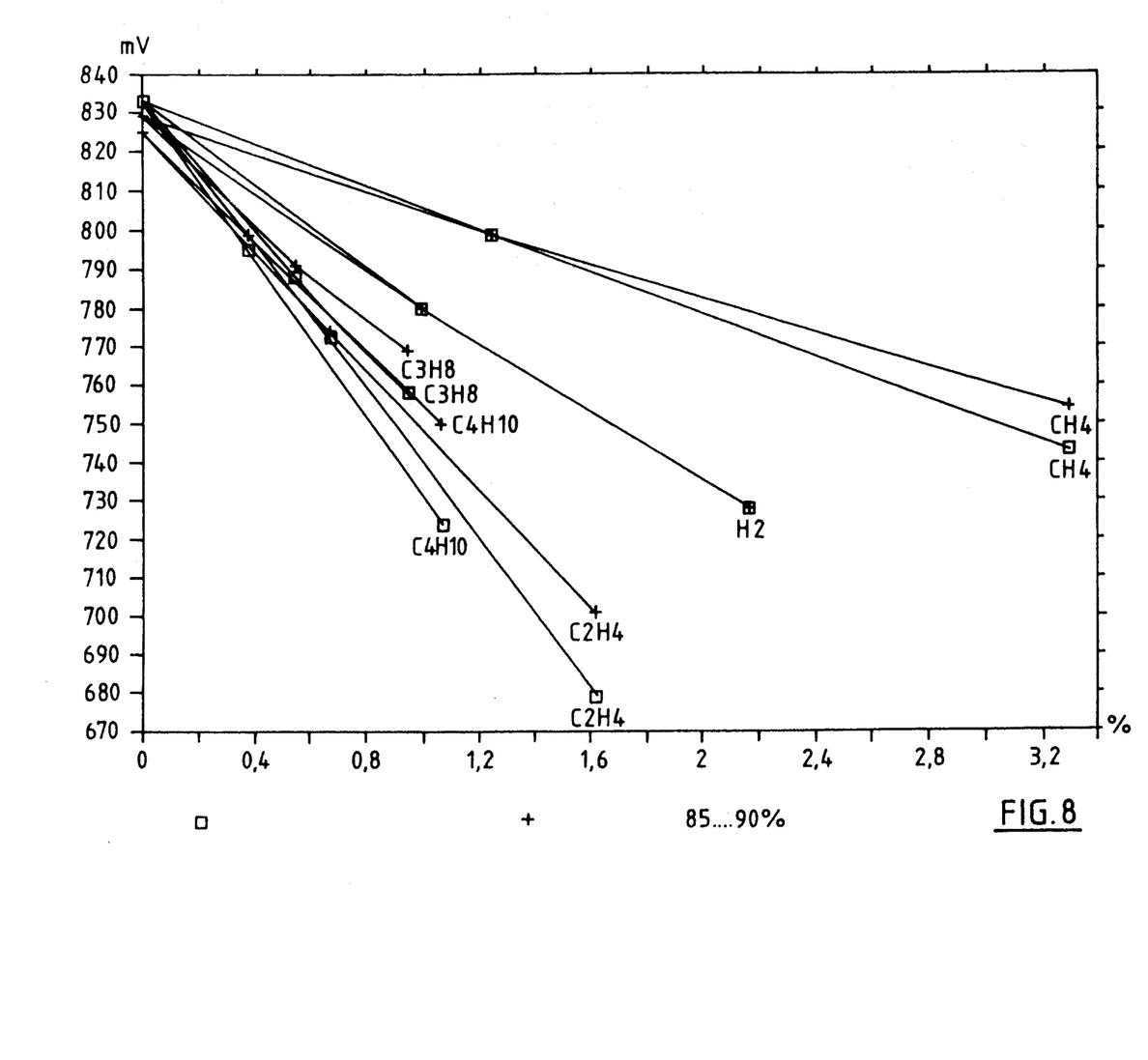
FIG. 8 is a graphical representation for an 80 μm diameter filament of the correlations between the response (in millivolts) of the detector and the actual concentration in the case of five gases, in the case of dry air (squares) and in the case of air with a relative humidity of 85 to 90% (crosses)

FIG. 8 shows the response in millivolts of the detector as a function of the actual concentration of five gases; methane, propane, butane, ethylene and hydrogen for two limiting values of relative humidity (dry air and moist air with a relative humidity of 85-90%).

Figure 9:
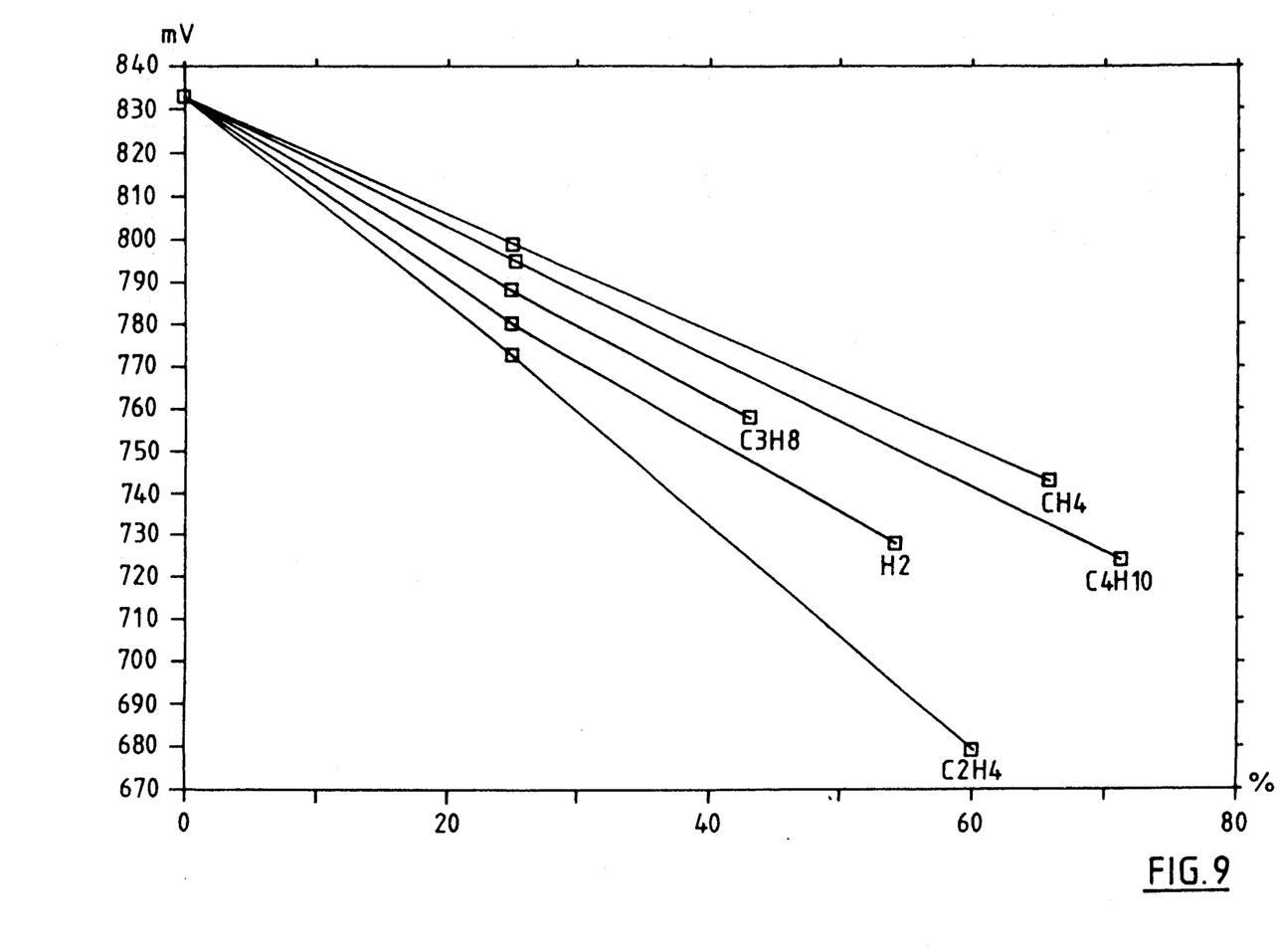
FIG. 9 is a graphical representation for the same type of filament and for the same gases of the correlations between the response (in millivolts) of the detector and the concentration of the gas expressed as a percentage of its lower explosibility limit in dry air.

FIG. 9 shows the response of the detector as a function of the concentration of the gas expressed as a percentage of the lower explosibility limit (LEL); a signal of 760 mV represents lower limits of explosivity of 54% or 30% depending on whether the explosible gas is methane or ethylene. This kind of error can be corrected in two ways, neither of which is satisfactory;

the apparatus can be calibrated to a specific gas that is to be detected but it must be recalibrated to measure a different gas, the apparatus can instead be calibrated to the gas for which the detector is least sensitive (methane in this example) but it is then necessary to take precautions out of all proportion to the actual hazard associated with other less sensitive gases.

The time for the detector to reach thermal equilibrium may be used to identify the nature of the gas; the user is therefore alerted to the actual hazard of explosion.

The time for the detector to reach thermal equilibrium is measured by means of a conventional signal processing technique which identifies maxima in the signal as a whole.

The sudden voltage drop characteristic of the time $t_2$ can instead be detected by an electronic comparator which activates an input of the microcontroller.

Figure 10:
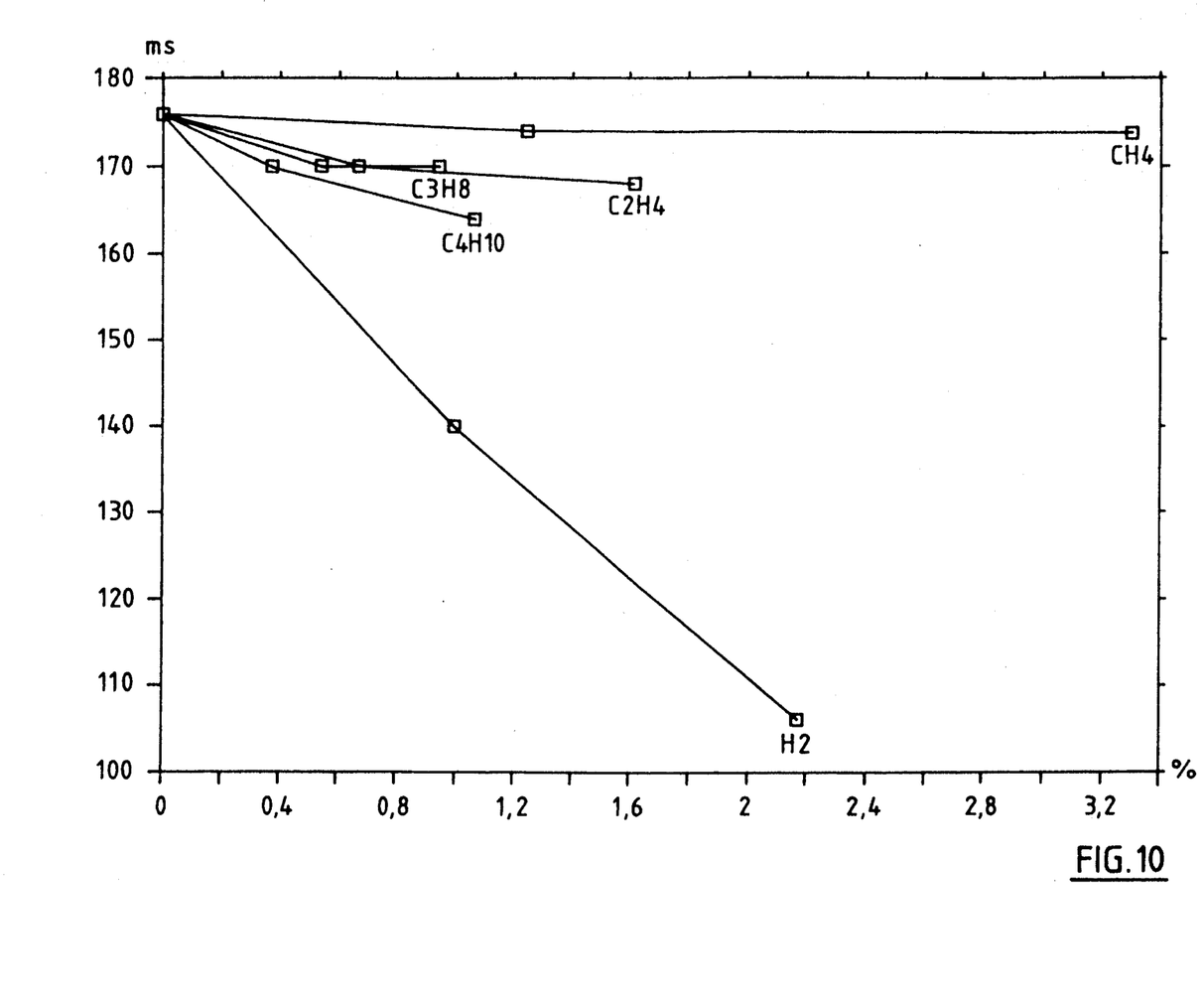
FIG. 10 is a graphical representation for the same type of filament and for the same gases of the correlations between the time for the detector to reach thermal equilibrium and the actual concentration of these gases in air, in the case of dry air.
Figure 11:
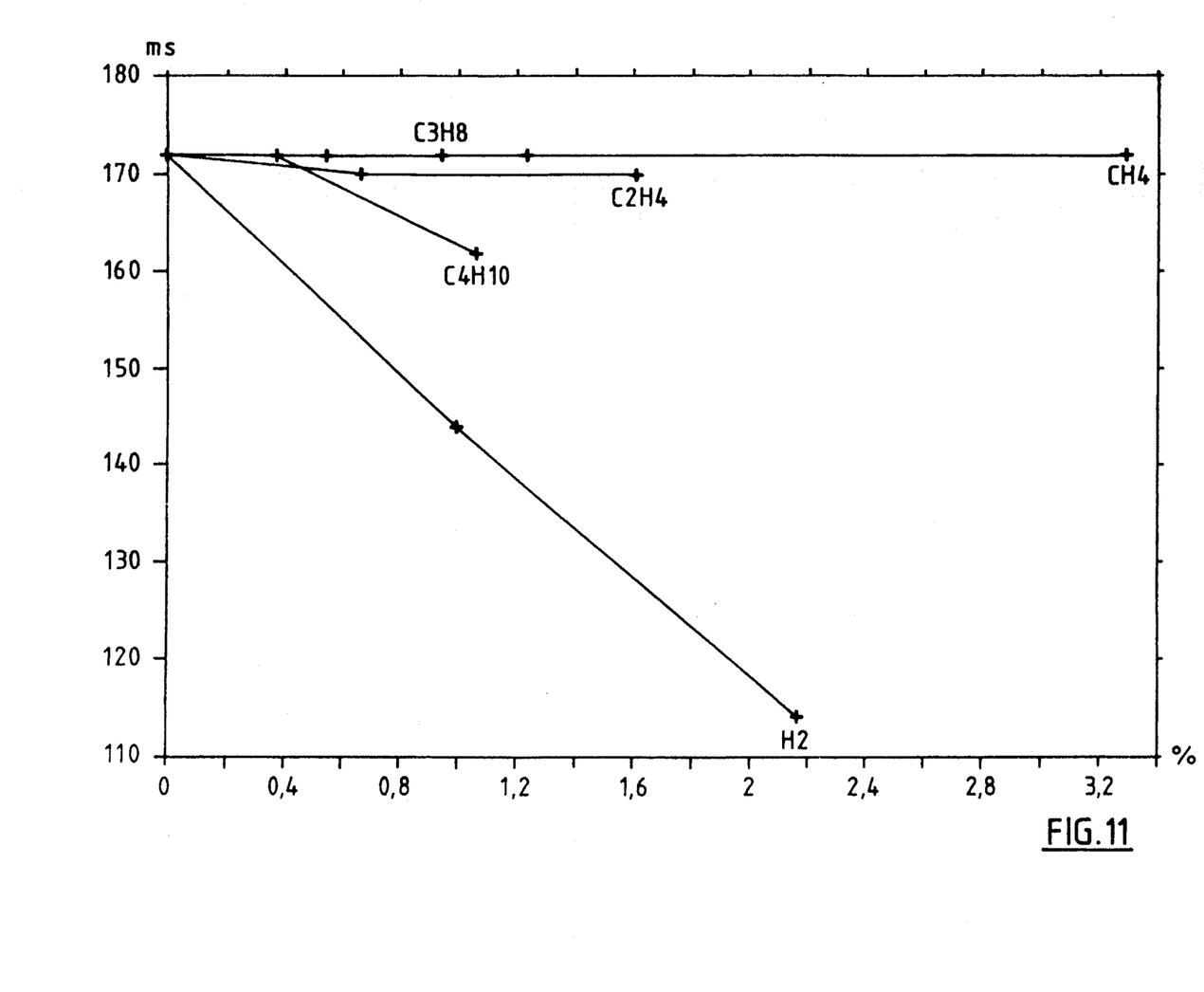
FIG. 11 is a diagram analogous to FIG. 10 for moist air.

FIGS. 10 and 11 show the time to reach thermal equilibrium as a function of the actual concentration of five gases for dry air and moist air; it is seen that it is possible to characterize each gas in this way.

Figure 12:
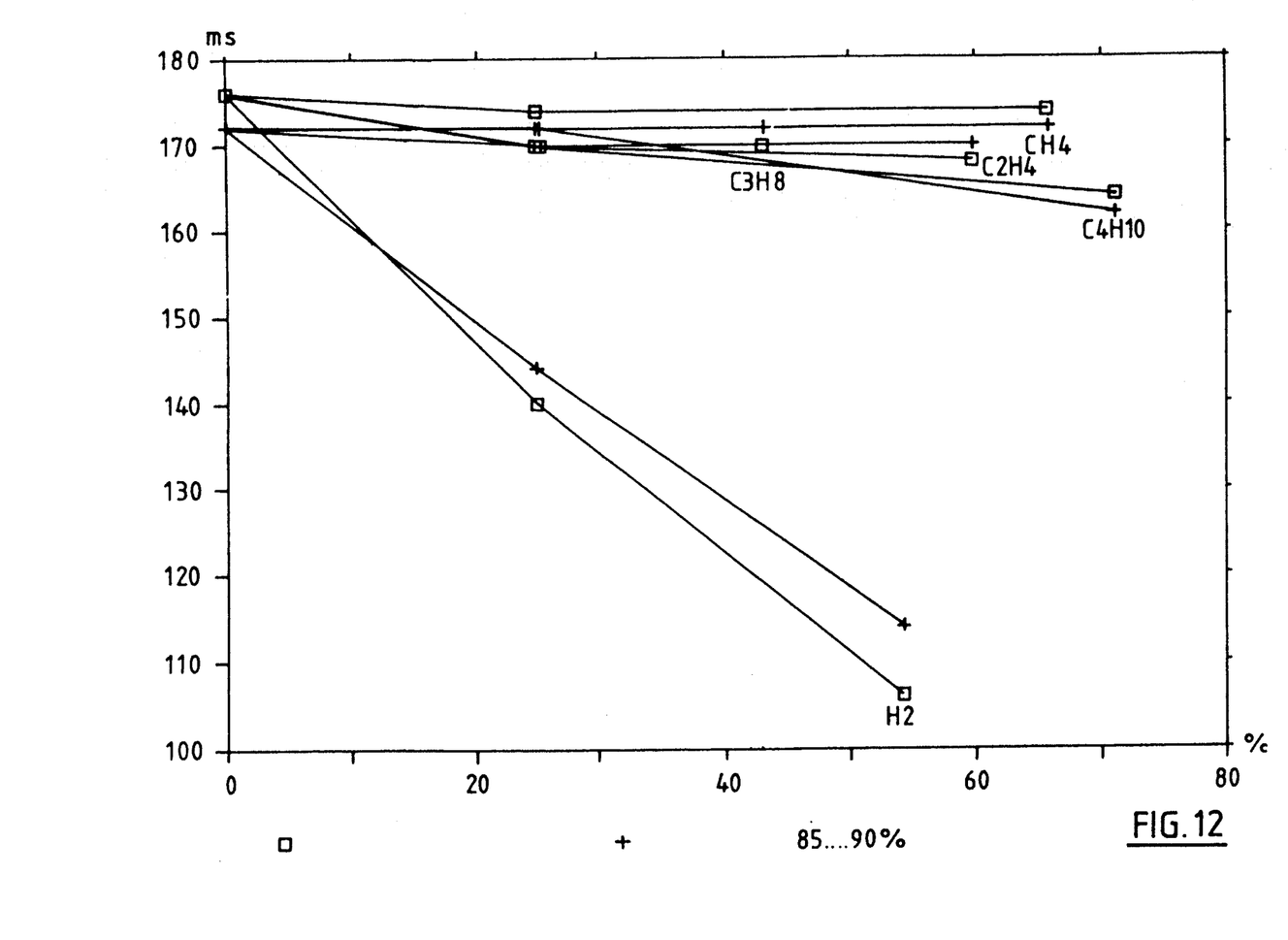
FIG. 12 is a graphical representation for the same type of filament and for the same gases of the correlations between the time for the detector to reach thermal equilibrium and the concentration of these gases expressed as a percentage of the lower explosibility limit in the case of dry air (squares) and in the case of moist air (crosses)

FIG. 12 shows the relationship between the time to reach thermal equilibrium and the response of the detector expressed as a percentage of the lower explosibility limit for various gases in dry air and in moist air (note the weak influence of the moisture content of the air on the time for the detector to reach thermal equilibrium).

Figure 13:
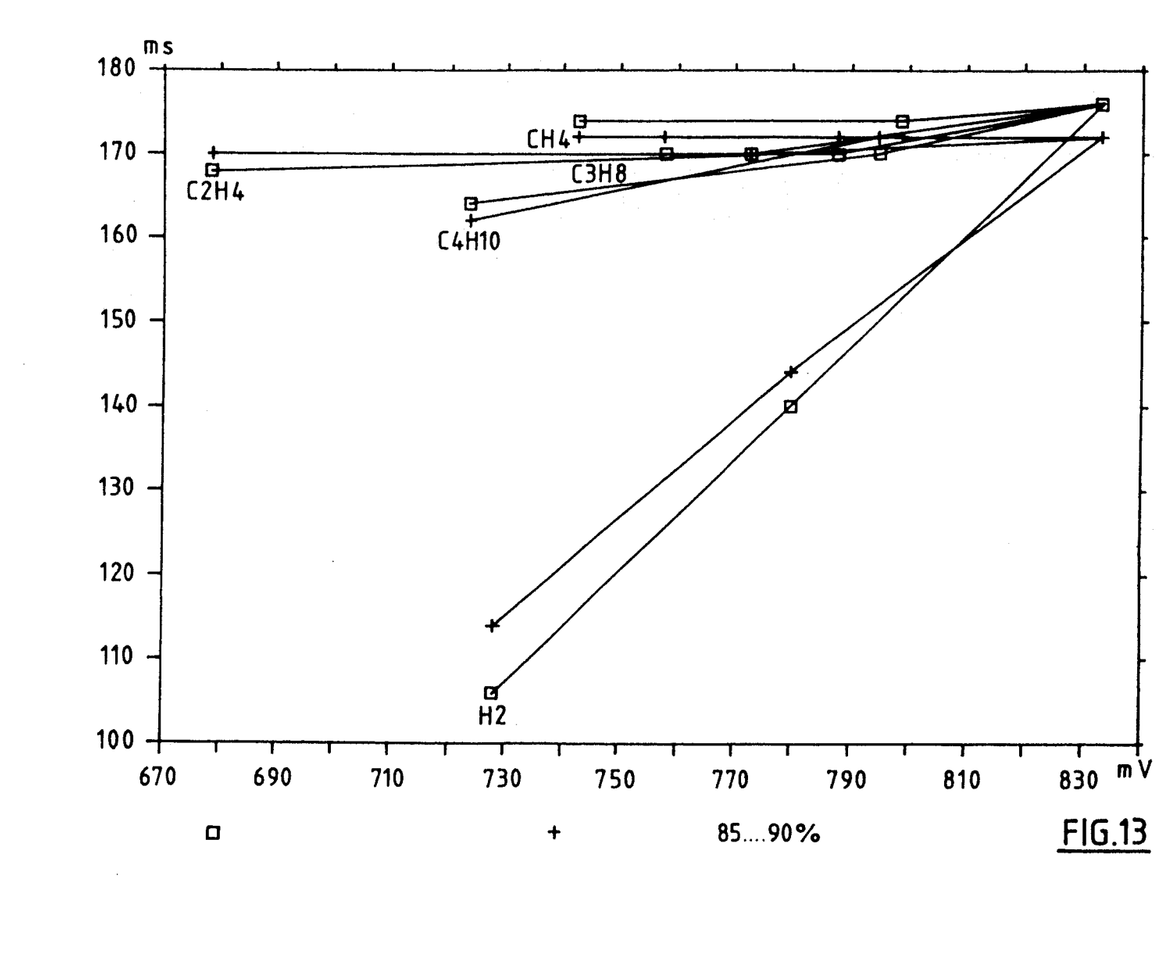
FIG. 13 is a graphical representation for the same type of filament and for the same gases of the correlations between the time for the detector to reach thermal equilibrium and the response (in millivolts) of the detector in the case of dry air (squares) and moist air (crosses).

The gas is identified by measuring the time to reach thermal equilibrium and the signal (in mV) across the filament (see FIG. 13); this pair of values corresponds to a point on one of the curves if the gas is a member of the family covered by the program in the microcontroller.

The use of this technique entails the processing of information by a microcontroller. On the basis of the voltage signal across the filament, the microcontroller can show the user the gas concentration on an alphanumeric display, its nature being identified by measuring the time to reach thermal equilibrium.

The microcontroller holds in read-only memory the data needed to recognize the gases deduced from FIG. 12.

The microcontroller 4 can be programmed to carry out the comparison, recognition and display operations necessary to use the apparatus.

It goes without saying that numerous variant embodiments may be suggested by those skilled in the art without departing from the scope of the invention, with regard both to the filament and to the processing electronics. Similarly, the experimental parameters may be chosen from a wide range of values (temperature or filament resistance).

Generally speaking, the method may equally well be applied to any detector operating discontinuously at a certain temperature. The invention therefore finds applications in a vast field through the association with the method, after the measurement has been obtained, of various forms of signal processing for purposes of display, transmission or storage and to trigger an alarm if a threshold is exceeded.

The invention is generally usable in applications including in particular the implementation of gas chromatography sensors.

We claim:

1. A method for measuring the concentration of a known combustible gas in a gaseous medium comprising,
    providing a resistive element having a catalytic surface being sensitive to concentration of known combustible gas,
    measuring a parameter of said resistive element representative of said concentration of known combustible gas, and
    determining from said parameter, a measurement of said concentration of known combustible gas based upon a predetermined calibration,
    wherein said measuring occurs during a predetermined interrogation period where said resistive element is supplied with power in cycles comprising three phases:
        in a first phase, a heating current flows in the resistive element at an intensity to raise temperature of the resistive element within a predetermined heating time to a predetermined set point temperature at which the catalytic surface of said resistive element catalyzes combustion of said combustible gas,
        in a second phase, the resistive element is supplied with an electric current for a predetermined period of time during which an intensity of said electric current is controlled so as to maintain the temperature of the resistive element at the predetermined set point temperature, and when a voltage $U_D$ across the resistive element has stabilized, a value of said parameter representative of said concentration of known combustible gas is measured, a power of said electric current being substantially less than a power of said heating current, and
        in a third phase, the electric current is reduced to allow said resistive element to cool to a quiescent temperature.

2. A method according to claim 13, wherein the predetermined interrogation period is not more than four seconds.

3. A method according to claim 2, wherein a total duration of the first and second phases is less than 300 ms.

4. A method according to claim 3, wherein a duration of the first phase is less than 200 ms.

5. A method according to claim 13, wherein the resistive element is platinum-based and itself a catalyst, and the predetermined set point temperature is between 570° C. and 1,100° C.

6. A method according to claim 13, wherein the set point temperature is substantially equal to 1,000° C.

7. A method according to claim 13, wherein an average power of said heating current is between one and three times the power of said electric current for the second phase.

8. A method according to claim 13, wherein said intensity is constant during the heating phase.

9. A method according to claim 13, wherein said power is interrupted during the third phase.

10. A method according to claim 13, wherein a ratio of the second phase temperature of the resistive element to the third phase temperature of the resistive element is between 1:1.1 and 1:4.

11. A method according to claim 13, wherein said parameter representative of the gas concentration is a resistance of the resistive element.

12. A method according to claim 1 wherein a chemical compound of said known combustible gas is determined by measuring time for said resistive element to reach thermal equilibrium based upon the predetermined calibration.

* * * * *